United States Patent
Pandey et al.

(10) Patent No.: US 10,444,638 B2
(45) Date of Patent: Oct. 15, 2019

(54) METHOD FOR PARAMETER DETERMINATION AND APPARATUS THEREOF

(71) Applicant: ASML Netherlands B.V., Veldhoven (NL)

(72) Inventors: Nitesh Pandey, Eindhoven (NL); Maxim Pisarenco, Son en Breugel (NL); Alessandro Polo, Delft (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/042,302

(22) Filed: Jul. 23, 2018

(65) Prior Publication Data

US 2019/0033725 A1 Jan. 31, 2019

Related U.S. Application Data (60) Provisional application No. 62/536,675, filed on Jul. 25, 2017.

(51) Int. Cl.
| | | |
|---|---|---|
| *G01N 21/00* | (2006.01) | |
| *G03F 7/20* | (2006.01) | |
| *G01N 21/956* | (2006.01) | |
| *G01N 29/06* | (2006.01) | |

(52) U.S. Cl.
CPC ... *G03F 7/70625* (2013.01); *G01N 21/95607* (2013.01); *G01N 29/0681* (2013.01); *G03F 7/70633* (2013.01); *G03F 7/70666* (2013.01)

(58) Field of Classification Search
CPC ...... G01N 21/956; G01N 29/00; G01N 29/06; G03F 7/20; G03F 7/70; C04B 35/00
See application file for complete search history.

(56) References Cited

U.S. PATENT DOCUMENTS

| | | | |
|---|---|---|---|
| 5,229,872 A | 7/1993 | Mumola | |
| 5,296,891 A | 3/1994 | Vogt et al. | |
| 5,523,193 A | 6/1996 | Nelson | |
| 6,952,253 B2 | 10/2005 | Lof et al. | |
| 7,701,577 B2 | 4/2010 | Straaijer et al. | |

(Continued)

FOREIGN PATENT DOCUMENTS

| | | |
|---|---|---|
| EP | 1 628 164 A2 | 2/2006 |
| WO | WO 99/49504 A1 | 9/1999 |
| WO | WO 2008/097527 A1 | 8/2008 |
| WO | WO 2011/012624 A1 | 2/2011 |

OTHER PUBLICATIONS

Li et al., "Attenuation of 7 GHz surface acoustic waves on silicon," American Physical Society, Physical Review B, vol. 94, Sep. 26, 2016; pp. 1-27.

(Continued)

*Primary Examiner* — Abdullahi Nur
(74) *Attorney, Agent, or Firm* — Sterne, Kessler, Goldstein & Fox P.L.L.C.

(57) ABSTRACT

A method and apparatus to measure overlay from images of metrology targets, images obtained using acoustic waves, for example images obtained using an acoustic microscope. The images of two targets are obtained, one image using acoustic waves and one image using optical waves, the edges of the images are determined and overlay between the two targets is obtained as the difference between the edges of the two images.

13 Claims, 4 Drawing Sheets

(56) References Cited

U.S. PATENT DOCUMENTS

| | | |
|---|---|---|
| 7,791,724 B2 | 9/2010 | Den Boef et al. |
| 8,115,926 B2 | 2/2012 | Straaijer |
| 8,553,227 B2 | 10/2013 | Jordanoska |
| 8,681,312 B2 | 3/2014 | Straaijer |
| 8,692,994 B2 | 4/2014 | Straaijer |
| 8,792,096 B2 | 7/2014 | Straaijer |
| 8,797,554 B2 | 8/2014 | Straaijer |
| 8,823,922 B2 | 9/2014 | Den Boef |
| 2010/0328655 A1 | 12/2010 | Den Boef |
| 2011/0026032 A1 | 2/2011 | Den Boef et al. |
| 2011/0036171 A1* | 2/2011 | Maris ............... G01N 29/0681 73/606 |
| 2011/0102753 A1 | 5/2011 | Van De Kerkhof et al. |
| 2011/0249244 A1 | 10/2011 | Leewis et al. |
| 2012/0044470 A1 | 2/2012 | Smilde et al. |
| 2013/0162996 A1 | 6/2013 | Straaijer et al. |
| 2013/0208279 A1 | 8/2013 | Smith |
| 2016/0161863 A1 | 6/2016 | Den Boef et al. |

OTHER PUBLICATIONS

Quate et al., "Acoustic Microscopy with Mechanical Scanning—A Review," Proceedings of the IEEE, vol. 67, No. 8, Aug. 1979; 36 pages.

International Search Report and Written Opinion of the International Searching Authority directed to related International Patent Application No. PCT/EP2018/069615, dated Oct. 10, 2018; 15 pages.

Arkalgud et al., "Frontiers of Characterization and Metrology for Nanoelectronics: Overview of 3D Integration Requirements," SEMATECH, 3D Interconnect Development, May 13, 2009; 24 pages.

Kong et al., "Sub-imaging Techniques for 3D-Interconnects on Bonded Wafer Pairs," CP1300 Stressed-Induced Phenomena in Metallization: 11$^{th}$ International Workshop, American Institute of Physics, 2010; pp. 221-228.

\* cited by examiner

METHOD FOR PARAMETER DETERMINATION AND APPARATUS THEREOF

CROSS REFERENCE TO RELATED APPLICATIONS

This application incorporates by reference in its entirety U.S. provisional application 62/536,675, filed Jul. 25, 2018.

FIELD

The present disclosure relates to methods and apparatus for inspection (e.g., metrology) usable, for example, in the manufacture of devices by lithographic techniques and to methods of manufacturing devices using lithographic techniques.

BACKGROUND

A lithographic apparatus is a machine constructed to apply a desired pattern onto a substrate. A lithographic apparatus can be used, for example, in the manufacture of integrated circuits (ICs). A lithographic apparatus may, for example, project a pattern (also often referred to as "design layout" or "design") at a patterning device (e.g., a mask) onto a layer of radiation-sensitive material (resist) provided on a substrate (e.g., a wafer).

To project a pattern on a substrate a lithographic apparatus may use electromagnetic radiation. The wavelength of this radiation determines the minimum size of features which can be formed on the substrate. Typical wavelengths currently in use are 365 nm (i-line), 248 nm, 193 nm and 13.5 nm. A lithographic apparatus, which uses extreme ultraviolet (EUV) radiation, having a wavelength within the range 4-20 nm, for example 6.7 nm or 13.5 nm, may be used to form smaller features on a substrate than a lithographic apparatus which uses, for example, radiation with a wavelength of 193 nm.

Low-k1 lithography may be used to process features with dimensions smaller than the classical resolution limit of a lithographic apparatus. In such process, the resolution formula may be expressed as $CD=k1\times\lambda/NA$, where $\lambda$ is the wavelength of radiation employed, NA is the numerical aperture of the projection optics in the lithographic apparatus, CD is the "critical dimension" (generally the smallest feature size printed, but in this case half-pitch) and k1 is an empirical resolution factor. In general, the smaller k1 the more difficult it becomes to reproduce the pattern on the substrate that resembles the shape and dimensions planned by a circuit designer in order to achieve particular electrical functionality and performance. To overcome these difficulties, sophisticated fine-tuning steps may be applied to the lithographic projection apparatus and/or design layout. These include, for example, but not limited to, optimization of NA, customized illumination schemes, use of phase shifting patterning devices, various optimization of the design layout such as optical proximity correction (OPC, sometimes also referred to as "optical and process correction") in the design layout, or other methods generally defined as "resolution enhancement techniques" (RET). Alternatively, tight control loops for controlling a stability of the lithographic apparatus may be used to improve reproduction of the pattern at low k1.

Thus in patterning processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of accuracy of alignment of two layers in a device. Overlay may be described in terms of the degree of misalignment between the two layers, for example reference to a measure overlay of 1 nm describe a situation where two layers are misaligned by 1 nm.

Various forms of inspection apparatus (e.g., metrology apparatus) have been developed for use in the lithographic field. These devices direct a beam of radiation onto a target and measure one or more properties of the redirected (e.g., scattered) radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

SUMMARY

A method and apparatus to measure overlay from images of metrology targets, images obtained using acoustic waves, for example images obtained using an acoustic microscope. A metrology apparatus comprising a source for generating acoustic waves. A method comprising measuring a parameter of a patterning process using acoustic waves, further comprising a first image of a first target is obtained using acoustic waves, a second image of a second target is obtained using optical waves, a characteristic of the first image and of the second image is determined and a parameter of the patterning process is determined as a difference between the characteristic of the first image and the characteristic of the second image. The characteristic is the edge of the image.

BRIEF DESCRIPTION OF THE DRAWINGS

Embodiments of the invention will now be described, by way of example only, with reference to the accompanying schematic drawings, in which.

DETAILED DESCRIPTION

In the present document, the terms "radiation" and "beam" are used to encompass all types of electromagnetic radiation, including ultraviolet radiation (e.g. with a wavelength of 365, 248, 193, 157 or 126 nm) and EUV (extreme ultra-violet radiation, e.g. having a wavelength in the range of about 5-100 nm).

The term "reticle", "mask" or "patterning device" as employed in this text may be broadly interpreted as referring to a generic patterning device that can be used to endow an incoming radiation beam with a patterned cross-section, corresponding to a pattern that is to be created in a target portion of the substrate; the term "light valve" can also be used in this context. Besides the classic mask (transmissive or reflective; binary, phase-shifting, hybrid, etc.), examples of other such patterning devices include:

a programmable mirror array. More information on such mirror arrays is given in U.S. Pat. Nos. 5,296,891 and 5,523,193, which are incorporated herein by reference.

a programmable LCD array. An example of such a construction is given in U.S. Pat. No. 5,229,872, which is incorporated herein by reference.

Figure 1:
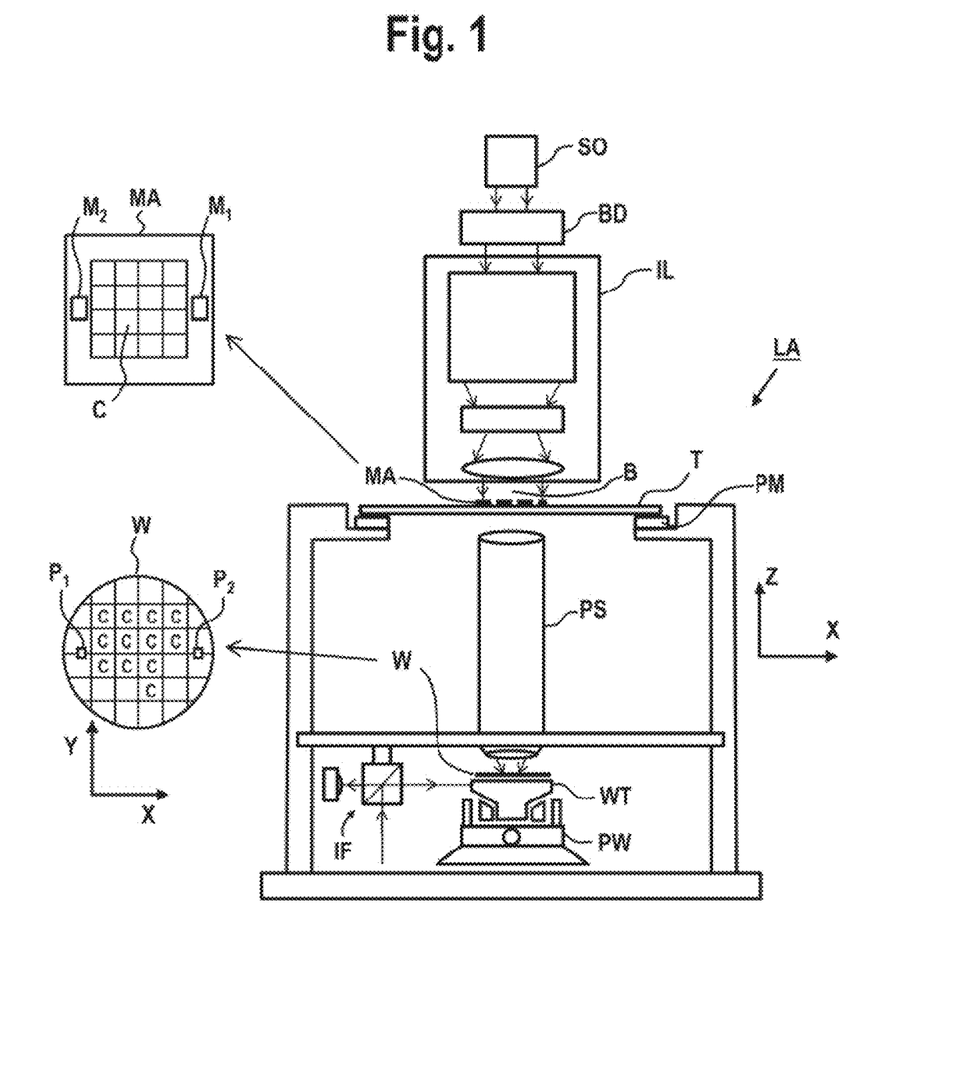
FIG. 1 depicts a schematic overview of a lithographic apparatus.

FIG. 1 schematically depicts a lithographic apparatus LA. The lithographic apparatus LA includes an illumination system (also referred to as illuminator) IL configured to condition a radiation beam B (e.g., UV radiation, DIN radiation or EUV radiation), a support structure (e.g., a mask table) T constructed to support a patterning device (e.g., a mask) MA and connected to a first positioner PM configured to accurately position the patterning device MA in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

In operation, the illuminator IL receives a radiation beam from a radiation source SO, e.g. via a beam delivery system BI). The illumination system IL may include various types of optical components, such as refractive, reflective, magnetic, electromagnetic, electrostatic, or other types of optical components, or any combination thereof, for directing, shaping, or controlling radiation. The illuminator IL may be used to condition the radiation beam B to have a desired spatial and angular intensity distribution in its cross section at a plane of the patterning device MA.

The term "projection system" PS used herein should be broadly interpreted as encompassing various types of projection system, including refractive, reflective, catadioptric, anamorphic, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system" PS.

The lithographic apparatus may be of a type wherein at least a portion of the substrate may be covered by a liquid having a relatively high refractive index, e.g., water, so as to fill a space between the projection system and the substrate which is also referred to as immersion lithography. More information on immersion techniques is given in U.S. Pat. No. 6,952,253 and in KT publication No. WO99-49504, which are incorporated herein by reference.

The lithographic apparatus LA may also be of a type having two (dual stage) or more substrate tables WI and, for example, two or more support structure T (not shown). In such "multiple stage" machines the additional tables/structures may be used in parallel, or preparatory steps may be carried out on one or more tables while one or more other tables are being used for exposing the design layout of the patterning device MA onto the substrate W.

In operation, the radiation beam B is incident on the patterning device (e.g., mask MA), which is held on the support structure (e.g., mask table T), and is patterned by the patterning device MA. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and possibly another position sensor (which is not explicitly depicted in FIG. 1) may be used to accurately position the mask MA with respect to the path of the radiation beam B. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks).

Figure 2:
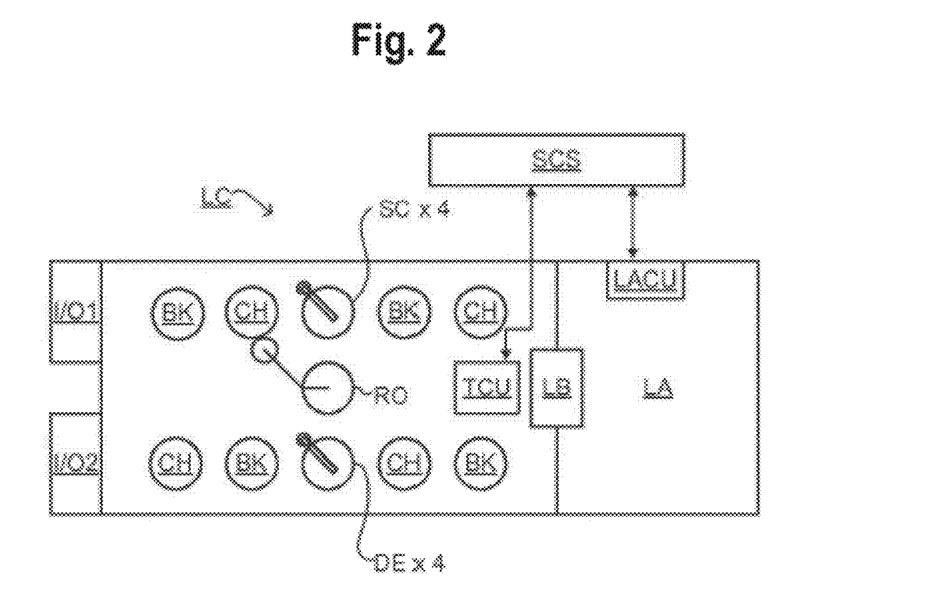
FIG. 2 depicts a schematic overview of a lithographic cell.

As shown in FIG. 2 the lithographic apparatus LA may form part of a lithographic cell LC, also sometimes referred to as a lithocell or (litho)cluster, which often also includes apparatus to perform pre- and post-exposure processes on a substrate W. Conventionally these include spin coaters SC to deposit resist layers, developers DE to develop exposed resist, chill plates CH and bake plates BK, e.g. for conditioning the temperature of substrates W e.g. for conditioning solvents in the resist layers. A substrate handler, or robot, RO picks up substrates W from input/output ports I/O1, I/O2, moves them between the different process apparatus and delivers the substrates W to the loading bay LB of the lithographic apparatus LA. The devices in the lithocell, which are often also collectively referred to as the track, are typically under the control of a track control unit TCU that in itself may be controlled by a supervisory control system SCS, which may also control the lithographic apparatus LA, e.g. via lithography control unit LACU.

In order for the substrates W exposed by the lithographic apparatus LA to be exposed correctly and consistently, it is desirable to inspect substrates to measure properties of patterned structures, such as overlay errors between subsequent layers, line thicknesses, critical dimensions (CD), etc. For this purpose, inspection tools (not shown) may be included in the lithocell LC. If errors are detected, adjustments, for example, may be made to exposures of subsequent substrates or to other processing steps that are to be performed on the substrates W, especially if the inspection is done before other substrates W of the same batch or lot are still to be exposed or processed.

An inspection apparatus, which may also be referred to as a metrology apparatus, is used to determine properties of the substrates W, and in particular, how properties of different substrates W vary or how properties associated with different layers of the same substrate W vary from layer to layer. The inspection apparatus may alternatively be constructed to identify defects on the substrate W and may, for example, be part of the lithocell LC, or may be integrated into the lithographic apparatus LA, or may even be a stand-alone device. The inspection apparatus may measure the properties on a latent image (image in a resist layer after the exposure), or on a semi-latent image (image in a resist layer after a post-exposure bake step PEB), or on a developed resist image (in which the exposed or unexposed parts of the resist have been removed), or even on an etched image (after a pattern transfer step such as etching).

Figure 3:
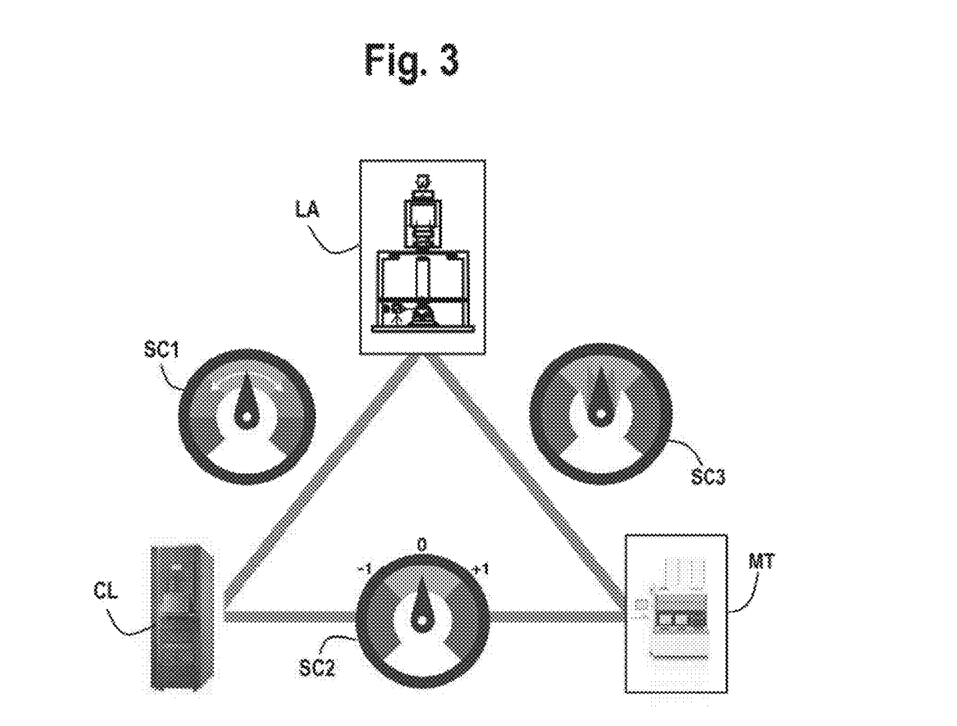
FIG. 3 depicts a schematic representation of holistic lithography, representing a cooperation between three key technologies to optimize semiconductor manufacturing.

Typically the patterning process in a lithographic apparatus LA is one of the most critical steps in the processing which requires high accuracy of dimensioning and placement of structures on the substrate W. To ensure this high accuracy, three systems may be combined in a so called "holistic" control environment as schematically depicted in FIG. 3. One of these systems is the lithographic apparatus LA which is (virtually) connected to a metrology tool MT (a second system) and to a computer system CL (a third system). The key of such "holistic" environment is to optimize the cooperation between these three systems to enhance the overall process window and provide tight control loops to ensure that the patterning performed by the lithographic apparatus LA stays within a process window. The process window defines a range of process parameters (e.g. dose, focus, overlay) within which a specific manufacturing process yields a defined result (e.g. a functional semiconductor device)—typically within which the process parameters in the lithographic process or patterning process are allowed to vary.

The computer system CL may use (part of) the design layout to be patterned to predict which resolution enhancement techniques to use and to perform computational lithography simulations and calculations to determine which mask layout and lithographic apparatus settings achieve the largest overall process window of the patterning process (depicted in FIG. 3 by the double arrow in the first scale SC1). Typically, the resolution enhancement techniques are arranged to match the patterning possibilities of the lithographic apparatus LA. The computer system CL may also be used to detect where within the process window the lithographic apparatus LA is currently operating (e.g. using input from the metrology tool MT) to predict whether defects may be present due to e.g. sub-optimal processing (depicted in FIG. 3 by the arrow pointing "0" in the second scale SC2).

The metrology tool MT may provide input to the computer system CL to enable accurate simulations and predictions, and may provide feedback to the lithographic apparatus LA to identify possible drifts, e.g. in a calibration status of the lithographic apparatus LA (depicted in FIG. 3 by the multiple arrows in the third scale SC3).

In lithographic processes, it is desirable to make frequently measurements of the structures created, e.g., for process control and verification. Tools to make such measurement are typically called metrology tools MT. Different types of metrology tools MT for making such measurements are known, including scanning electron microscopes or various forms of scatterometer metrology tools MT. Scatterometers are versatile instruments which allow measurements of the parameters of a lithographic process by having a sensor in the pupil or a conjugate plane with the pupil of the objective of the scatterometer, measurements usually referred as pupil based measurements, or by having the sensor in the image plane or a plane conjugate with the image plane, in which case the measurements are usually referred as image or field based measurements. Such scatterometers and the associated measurement techniques are further described in patent applications US20100328655, US2011102753A1, US20120044470A, US20110249244, US20110026032 or EP1,628,164A, incorporated herein by reference in their entirety. Aforementioned scatterometers may measure gratings using light from soft x-ray and visible to near-IR wavelength range.

In a first embodiment, the scatterometer MT is an angular resolved scatterometer. In such a scatterometer reconstruction methods may be applied to the measured signal to reconstruct or calculate properties of the grating. Such reconstruction may, for example, result from simulating interaction of scattered radiation with a mathematical model of the target structure and comparing the simulation results with those of a measurement. Parameters of the mathematical model are adjusted until the simulated interaction produces a diffraction pattern similar to that observed from the real target.

In a second embodiment, the scatterometer MT is a spectroscopic scatterometer MT. In such spectroscopic scatterometer MT, the radiation emitted by a radiation source is directed onto the target and the reflected or scattered radiation from the target is directed to a spectrometer detector, which measures a spectrum (i.e. a measurement of intensity as a function of wavelength) of the specular reflected radiation. From this data, the structure or profile of the target giving rise to the detected spectrum may be reconstructed, e.g. by Rigorous Coupled Wave Analysis and non-linear regression or by comparison with a library of simulated spectra.

In a third embodiment, the scatterometer MT is a ellipsometric scatterometer. The ellipsometric scatterometer allows for determining parameters of a lithographic process by measuring scattered radiation for each polarization states. Such metrology apparatus emits polarized light (such as linear, circular, or elliptic) by using, for example, appropriate polarization filters in the illumination section of the metrology apparatus. A source suitable for the metrology apparatus may provide polarized radiation as well. Various embodiments of existing ellipsometric scatterometers are described in U.S. patent application Ser. Nos. 11/451,599, 11/708,678, 12/256,780, 12/486,449, 12/920,968, 12/922,587, 13/000,229, 13/033,135, 13/533,110 and 13/891,410 incorporated herein by reference in their entirety.

A further realization of a metrology tool is Image Based Overlay metrology tool, which is a measurement technique using optical (visible) radiation to determine overlay by detecting an image of a specially designed overlay target. Typical target for the Image Based Overlay (IBO) measurements are performed using targets, such as box-in-box or bar-in-bar targets. MO based measurements are further described in US patent application US20130208279, incorporated herein by reference in its entirety.

In one embodiment of the scatterometer MT, the scatterometer MT is adapted to measure the overlay of two misaligned gratings or periodic structures by measuring asymmetry in the reflected spectrum and/or the detection configuration, the asymmetry being related to the extent of the overlay. The two (typically overlapping) grating structures may be applied in two different layers (not necessarily consecutive layers), and may be formed substantially at the same position on the wafer. The scatterometer may have a symmetrical detection configuration as described e.g. in co-owned patent application EP1,628,164A, such that any asymmetry is clearly distinguishable. This provides a straightforward way to measure misalignment in gratings. Further examples for measuring overlay error between the two layers containing periodic structures as target is measured through asymmetry of the periodic structures may be found in PCT patent application publication no. WO2011/012624 or US patent application US 20160161863, incorporated herein by reference in its entirety.

In the fabrication of lithographic devices with enhanced 3 dimensional features, for example X-point memory or 3D NAND structures, an opaque layer is needed for assuring correct device processing. Typically, such layer is opaque to visible radiation, in particular configurations, depending on the application or the type of material used for the opaque layer, such layer is transmissive for infra-red radiation. Technology roadmaps predict, however, that layers which are hardly transmissive for optical radiation (in the visible spectrum or infra-red spectrum) are needed, with a strong preference for layers made of materials non-optically transmissive (e.g., metal layers). As a consequence, the determination of a property of interest of a patterning process may be performed by techniques which do not employ the use of visible or infra-red radiation.

The present disclosure describes a method to measure a parameter of a patterning process using acoustic waves or radiation. The present disclosure also describes a metrology apparatus comprising a source of generating acoustic waves. In an embodiment, the parameter of the patterning process is overlay. In an embodiment, the method to measure a parameter of a patterning process uses images of a metrology target obtained with acoustic based tools. An example of such acoustic imaging tools is a Surface Acoustic Microscope (SAM), and the principle of operation is described in C. F. Quate, A. Atalar, H. K. Wickramasinghe, published in Proceedings of the IEEE, vol. 67, no. 8, August 1979, which is herein incorporated by reference in its entirety.

In general, an acoustic wave penetrates a material depending on the acoustic properties of the material, also for cases where the material is not optical transmissive, such as in the case of a metal layer used in the fabrication of 3D NAND structures, for example. An acoustic microscope uses this principle to obtain images of structures which are buried inside materials, in an example of a grating buried in semiconductor layer stack. The depth at which an acoustic microscope measures images depends on the attenuation of the acoustic wave at the excitation frequency. The dependence on frequency is not straightforward. In metals, the main source of attenuation turns out to be 'thermoelastic heat flow', as explain in C. F. Quate et al, cited above, and the overall attenuation increases as a square of frequency. In insulators, the main source of attenuation is due to phonon gas induced collisions and damping. In semiconductors it can be expected to be a combination of these two effects. Typically attenuation seems to be proportional to the square of frequency of the acoustic wave, however, for extreme high acoustic frequencies e.g., several GHz), experimental results have shown a slower attenuation low, as disclosed in Li and Cahill, Phys. Rev. B 94, 104306, incorporated herein by reference in its entirety.

Thus, in order to obtain deeper penetration depth for the acoustic wave used to obtain images of a buried object in an acoustic microscope, object such as an overlay target, the frequency of the acoustic waves needs to be reduced and therefore the wavelength needs to be increased. The effect of this relationship of physical properties of the acoustic waves in a material indicates that deeper buried objects, such as a metrology target, need to have increased dimensions accordingly. In other words, the resolution of an image taken with an acoustic microscope decreases with the distance where the object is buried. In the semiconductor industry the metrology target are usually printed under several 100 nm to a couple of microns of opaque materials. Hence imaging with acoustic frequency up to several GHz is possible, potentially giving a spatial resolution in the micron or even sub-micron range.

In order to calibrate such effect, a calibration of the loss of reflected acoustic power with the depth of the material is needed, calibration also called V(z) curve. It represents the voltage detected at the acoustic transducer as a function of the de-focus—of the acoustic wave. The V(z) curve reveals important information on the surface of the sample and the underlying structure. As described in reference 35 cited in C. F. Quate et al above, the acoustic microscope is typically operated at a slight de-focus as the signals.

Figure 4A:
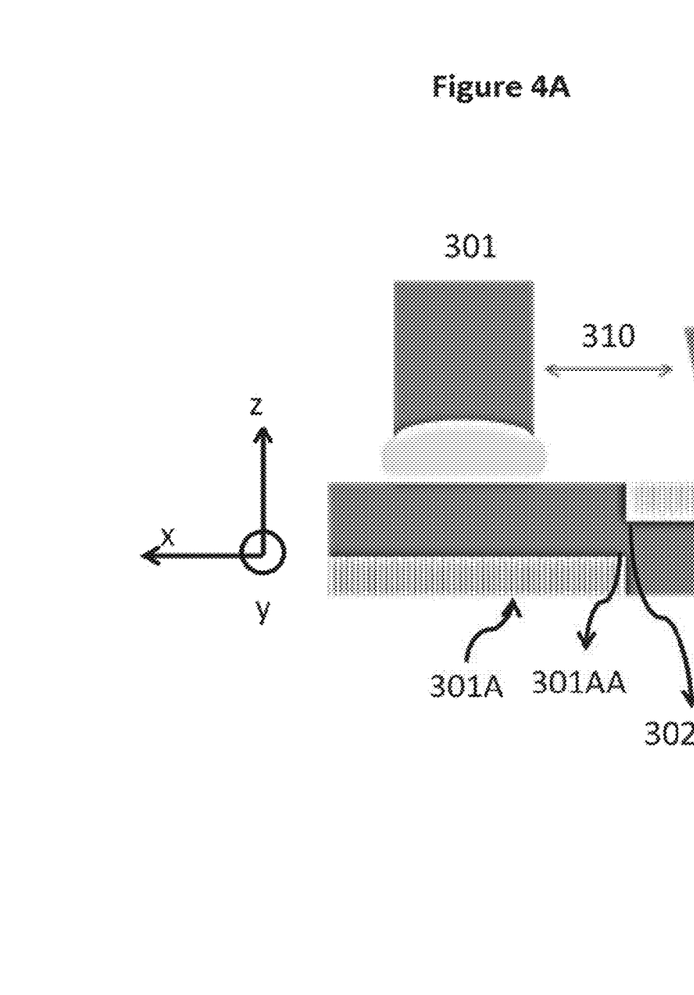
FIGS. 4A-4B depict in FIG. 4A an embodiment for an apparatus according to the current disclosure comprising an acoustic metrology apparatus and an optical metrology apparatus and in FIG. 4B an image of a measured overlay target.

A typical overlay target suitable for acoustic overlay measurements may consist of two adjacent gratings, such grating 301A of FIG. 4A (buried grating) and grating 302A of FIG. 4A (top grating). Grating 302A has dimensions between 1 micrometers and 10 micrometers pitch with duty cycle of 50%, for example. Grating 301A has dimension between 1 micrometer and 10 micrometers pitch, for example. It is assumed that for between these gratings a metal layer of 1 micrometer of W is present. Another example of an opaque layer is formed by several micrometers of amorphous Carbon.

Figure 4B:
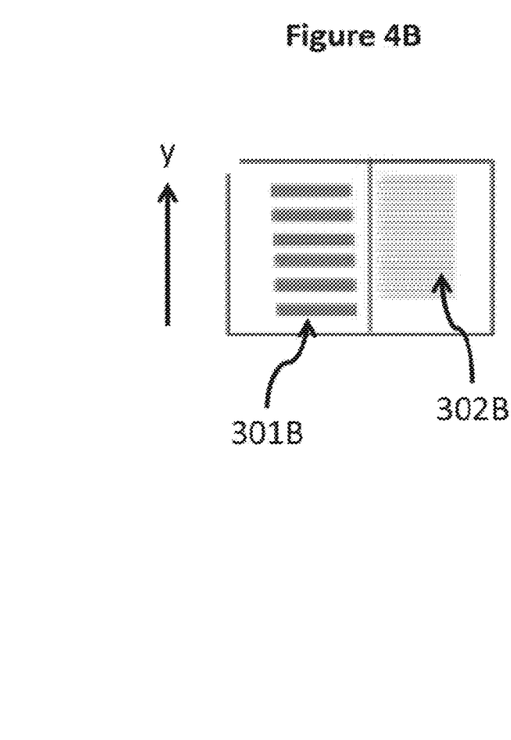

The acoustic microscope has an acoustic source which delivers acoustic waves having the frequency in the GHz ranges, for example the source has a frequency of 1 GHz, corresponding to a wavelength of 0.7 micrometers, and it has a Numerical Apertures of 0.5. In these conditions one can assume a resolution of about 1 micrometer on the surface of the substrate which needs to be imaged bye the acoustic microscope. The attenuation in the GHz regime for W is in the order of 2 dB/cm. For Ti it is 10 dB/cm and for Gold it is 100 dB/cm. Assuming a value of 50 dB/cm, roundtrip attenuation of metal film is still 5×10−4 dB/micrometer. Thus, in the GHz range, attenuation is not a significant problem and hence the bottom grating can be of the pitches as calculated above in the range of 5-10 um. Attenuation becomes a larger problem at higher frequencies as it is inversely proportional to square of frequency, although for GHz regime a lower than 2 power law could be expected. Images obtained with the metrology arrangement of FIG. 4A are shown in FIG. 4B, wherein 301B is the image of the bottom grating 301A and 302B is the image of the top grating 302A.

A hybrid metrology solution, comprising an acoustic microscope, such as 301 of FIG. 4A, and an optical microscope, such as 302 of FIG. 4A, tools which are separated by a distance 310, calibrated on the knowledge of, for example, size of the microscopes, the targets to be used, the speed of the substrate support table. In the example of FIG. 4A, the overlay is the relative distance as measured between the edges 301AA and 302AA as measured from the images of the gratings 301A and 302A.

In an embodiment, both gratings 301A and 302A of FIG. 4A are measured with an acoustic microscope. A measurement means an image of each grating is obtained, the edges 301AA and 302AA are obtained, and the overlay, is determined by the difference between the two edges 301AA and 302AA. The acoustic microscope measures the top grating 302A and the bottom grating 301A.

Figure 5:
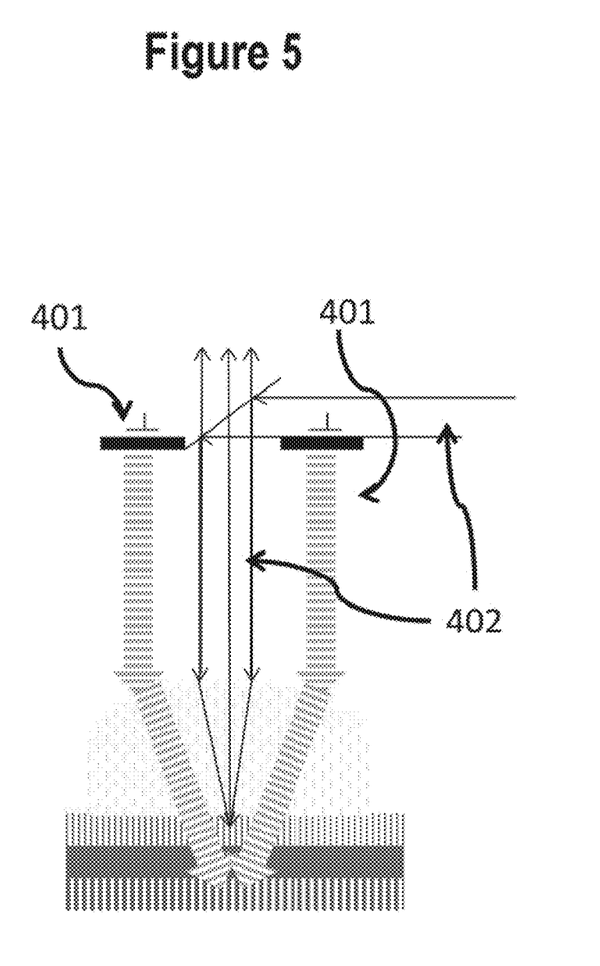
FIG. 5 depicts another embodiment according to the current disclosure of a combined acoustic and optical metrology apparatus.

In an embodiment, the same arrangement, which operates as a "lens" for an acoustic microscope, is modified to allow an optical arrangement, such as an optical objective, as can be seen in FIG. 5. The same lens can be used to focus optical radiation 402 and acoustic radiation 401. By fabricating a beam splitter on the acoustic lens the same lens can be used as an optical and acoustic lens. The material can be sapphire glass as it is transparent at optical wavelengths and is also used an acoustic lens. Overlay information is obtained by comparing the image obtained with optical means and the image obtained with acoustic means. The operation of the apparatus as shown in FIG. 5 is described in European patent application 18153587.3 incorporated herein by reference in its entirety.

The acoustic microscopes described in above embodiments may be further improved by modifying them to allow phase detection or to allow better coupling of the acoustic field into the target material. In an embodiment, a piezoelectric transducer scans a target emitting pulsed acoustic fields. The transmitted and the reflected echoes are collected which allows to reconstruct the image of the sample in a coherent manner. In this embodiment, both the amplitude and phase may be applied to signal processing. In another embodiment, the scanning acoustic microscope may be modified with a layer comprising a metamaterial which allows improved coupling of the spatial variations of the acoustic field which are equal or smaller than the operating wavelength of the acoustic microscope.

Although specific reference may be made in this text to the use of lithographic apparatus in the manufacture of it should be understood that the lithographic apparatus described herein may have other applications. Possible other applications include the manufacture of integrated optical systems, guidance and detection patterns for magnetic domain memories, flat-panel displays, liquid-crystal displays (LCDs), thin-film magnetic heads, etc.

Although specific reference may be made in this text to embodiments of the invention in the context of a lithographic apparatus, embodiments of the invention may be used in other apparatus. Embodiments of the invention may form part of a mask inspection apparatus, a metrology apparatus, or any apparatus that measures or processes an object such as a wafer (or other substrate) or mask (or other patterning device). These apparatus may be generally referred to as lithographic tools. Such a lithographic tool may use vacuum conditions or ambient (non-vacuum) conditions.

Although specific reference may have been made above to the use of embodiments of the invention in the context of optical lithography, it will be appreciated that the invention, where the context allows, is not limited to optical lithography and may be used in other applications, for example imprint lithography.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A method for measuring a parameter of a patterning process, comprising:
    obtaining a first image of a first target using acoustic waves;
    obtaining a second image of a second target using optical waves;
    determining a characteristic of the first image and a characteristic of the second image; and
    determining a difference between the characteristic of the first image and the characteristic of the second image to yield a parameter of the patterning process.

2. The method of claim 1, wherein the characteristic of at least one of the first image or the second image is the edge of the image.

3. The method of claim 1, wherein the parameter is overlay.

4. The method of claim 1, further comprising focusing the acoustic waves and the optical waves using an optical objective.

5. The method of claim 1, wherein the obtaining the first image is performed using an acoustic microscope.

6. The method of claim 1, further comprising scanning using the acoustic microscope to obtain the first image.

7. A apparatus for measuring a parameter of a patterning process, comprising:
    an acoustic device configured to obtain a first image of a first target using acoustic waves;
    an optical device configured to obtain a second image of a second target using optical waves; and
    wherein the apparatus is configured to:
        determine a characteristic of the first image and a characteristic of the second image; and
        determine a difference between the characteristic of the first image and the characteristic of the second image to yield a parameter of the patterning process.

8. The apparatus of claim 7, wherein the characteristic of at least one of the first image or the second image is the edge of the image.

9. The apparatus of claim 7, wherein the parameter is overlay.

10. The apparatus of claim 7, further comprising an optical objective configured to focus the acoustic waves and the optical waves.

11. The apparatus of claim 7, wherein the acoustic devices comprises an acoustic microscope.

12. The apparatus of claim 11, wherein the acoustic microscope is configured to perform scanning using a piezoelectric transducer.

13. The apparatus of claim 11, wherein the acoustic microscope comprises a metamaterial to improve coupling of spatial variations of an acoustic field that are equal or smaller than an operating wavelength of the acoustic microscope.

* * * * *